United States Patent [19]
Wood

[11] Patent Number: 6,012,814
[45] Date of Patent: Jan. 11, 2000

[54] EXTRAOCULAR MUSCLE TESTER

[75] Inventor: Mark G. Wood, Albuquerque, N.Mex.

[73] Assignee: University of New Mexico, Albuquerque, N.Mex.

[21] Appl. No.: 09/320,944

[22] Filed: May 26, 1999

Related U.S. Application Data

[60] Provisional application No. 60/087,093, May 28, 1998.

[51] Int. Cl.$^7$ .................................................. A61B 3/00
[52] U.S. Cl. .............................................................. 351/219
[58] Field of Search ..................................... 351/202, 205, 351/209, 210, 219, 221, 160 R, 161, 246, 247

[56] References Cited

U.S. PATENT DOCUMENTS

| | | |
|---|---|---|
| 3,507,988 | 4/1970 | Holmes . |
| 3,689,135 | 9/1972 | Young et al. . |
| 4,162,122 | 7/1979 | Cohen . |
| 4,212,226 | 7/1980 | Teltscher . |
| 4,637,697 | 1/1987 | Freeman . |
| 4,735,498 | 4/1988 | Uddén et al. . |
| 4,815,839 | 3/1989 | Waldorf . |
| 4,973,149 | 11/1990 | Hutchinson . |
| 4,995,714 | 2/1991 | Cohen . |
| 5,071,207 | 12/1991 | Ceglio et al. . |
| 5,104,212 | 4/1992 | Taboury et al. . |
| 5,270,748 | 12/1993 | Katz . |
| 5,298,927 | 3/1994 | Konishi et al. . |
| 5,345,281 | 9/1994 | Taboada et al. . |
| 5,386,258 | 1/1995 | Nagano . |
| 5,410,376 | 4/1995 | Cornsweet et al. . |
| 5,430,505 | 7/1995 | Katz . |
| 5,610,673 | 3/1997 | Rafal et al. . |
| 5,822,036 | 10/1998 | Massie ..................................... 351/219 |

Primary Examiner—George Manuel
Attorney, Agent, or Firm—Jagtiani & Associates

[57] ABSTRACT

In one embodiment, the present invention provides a method for measuring the movement of an individual's eye comprising the steps of: mounting a first infrared filter in a first eye of an individual, the first infrared filter filtering infrared light at a first wavelength; mounting a second infrared filter in the second eye of an individual, the second infrared filter filtering infrared light at a second wavelength; detecting infrared light of the first wavelength filtered by the first infrared filter by a first sub-array of photodetectors as the first eye of the individual rotates; and detecting infrared light of the second wavelength filtered by the second infrared filter by a second sub-array of photodetectors as the second eye of the individual rotates. The present invention also provides a contact lens comprising: a lens having a central clear zone; and at least one Fresnel ring circumferentially surrounding the central clear zone and filtering at least one wavelength of infrared light.

15 Claims, 3 Drawing Sheets

302

300

402

400

500

502

210

EXTRAOCULAR MUSCLE TESTER

CROSS-REFERENCE TO RELATED APPLICATIONS

The present application is based on Provisional Application No. 60/087,093 filed May 28, 1998, the entire disclosure and contents of which is hereby incorporated by reference.

BACKGROUND OF THE INVENTION

1. Field of the Invention

The present invention relates to extraocular muscle function testing.

2. Description of the Prior Art

In current methods of testing extraocular muscle functioning, measurements of the cardinal positions of gaze are non-calibrated. The measurements are typically taken in non-standardized environments and are dependent on hand held prisms that change dioptric prism power as the back surface of the prism varies from its perpendicular position relative to the surface of the eye. These measurements change from surgeon to surgeon and from room to room; are dependent on patient cooperation; and can be affected by fatigue on both the surgeon's and patient's part. Therefore, the currently used measurement methods are tedious, inaccurate, non-standardized, and patient and surgeon dependent.

SUMMARY OF THE INVENTION

It is therefore one object of the present invention to provide an extraocular muscle function testing method which has improved accuracy and range.

According to one aspect of the present invention, there is provided a method for measuring the movement of an individual's eye comprising the steps of: mounting a first infrared filter in a first eye of an individual, the first infrared filter filtering infrared light at a first wavelength; mounting a second infrared filter in the second eye of an individual, the second infrared filter filtering infrared light at a second wavelength; detecting infrared light of the first wavelength filtered by the first infrared filter by a first sub-array of photodetectors as the first eye of the individual rotates; and detecting infrared light of the second wavelength filtered by the second infrared filter by a second sub-array of photodetectors as the second eye of the individual rotates.

According to a second aspect of the invention, there is provided a contact lens comprising: a lens having a central clear zone; and at least one Fresnel ring circumferentially surrounding the central clear zone and filtering at least one wavelength of infrared light.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Definitions

For the purposes of the present invention, the term "individual" refers to either an individual person or animal whose eye movements are to be measured by the method of the present invention.

For the purposes of the present invention, the term "infrared filter" refers to Fresnel rings and gratings that filter light at a particular infrared wavelength.

For the purposes of the present invention, the term "Fresnel ring" refers to an annular zone which delays the phase of an optical beam by $2\pi$ radians at its thickest part.

For the purposes of the present invention the term "clear" when used to describe the central zone of a contact lens is used not only to describe a central zone that is clear in the conventional meaning of the word, but also a zone that has a color that does not interfere with practicing the method of the present invention. A portion of a contact lens is "clear" not only when it has no color, but also if it does not filter the same infrared wavelength as filtered by the Fresnel rings or other filter in the contact lens for either eye. For example, a contact lens used in the present invention may have a central zone that is tinted yellow, provided that the central zone does not filter the infrared wavelengths of interest filtered by the Fresnel rings in the contact lenses.

For the purposes of the present invention, the term "infrared wavelength" includes light having a wavelength of 0.7 $\mu$m to 1.2 $\mu$m.

Description

Figure 1A:
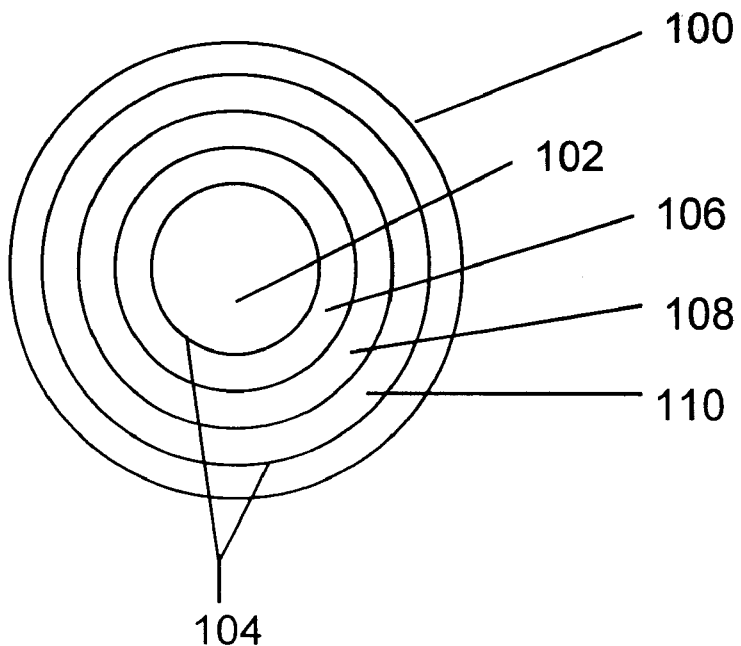
FIG. 1A illustrates in schematic form a contact lens of the present invention.
Figure 1B:
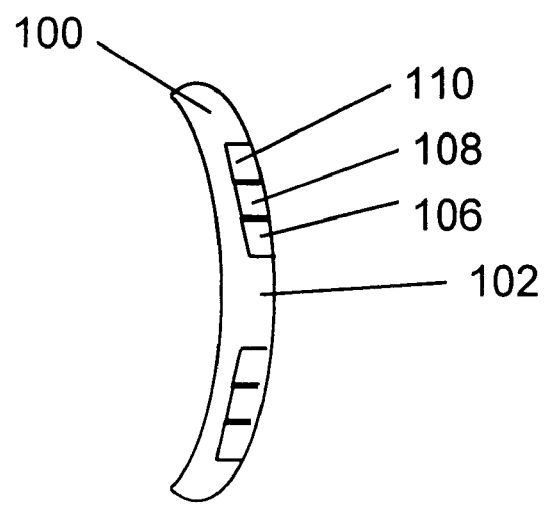
FIG. 1B is a schematic side view of the contact lens of FIG. 1A.

In the method of the present invention, the extraocular muscle functioning of an individual is tested by measuring the movement of the individual's eye. The individual being tested wears a comfortable, but tight fitting contact lens on each eye, similar to a conventional contact lens, preferably a soft contact lens. The soft contact lens used in each eye may be made from any conventional soft contact lens material. FIG. 1 illustrates such a lens 100 that includes an optically clear central zone 102. Surrounding central zone 102 is an exterior region 104 having three successive Fresnel rings 106, 108 and 110 which are embedded in lens 100 and act as filters for infrared light. These Fresnel rings may be formed by molding, etching or ruling. Typically, a lens of the present invention is about 12 to 14 mm in diameter, about the size of a conventional soft contact lens. Preferably, the central zone is about 4 mm in diameter. Preferably, the number of Fresnel rings is between 1 and 6. The set of Fresnel rings in each contact lens of each pair of contact lenses of the present invention are different, so that the Fresnel rings for the contact lens for an individual's right eye filters infrared light at one wavelength and the Fresnel rings in the contact lens on the individual's left eye filters infrared light at a second wavelength.

In order to measure the velocity of movement of each eye, an array of paired infrared photodetector devices is placed at a distance from an individual equal to the focal length of the Fresnel rings on the contact lenses in the individual's eyes, preferably ⅓ meter. Each paired photodetector device includes one photodetector for the infrared light filtered by the Fresnel rings of the contact lens for the right eye and a second photodetector for the infrared light filtered by the Fresnel rings of the contact lens for the left eye. Therefore, the array of photodetector devices can be viewed as two sub-arrays of photodetectors, one sub-array for each eye. The photodetector devices are preferably spaced 1 cm apart and the array of photodetector devices is preferably wide enough to measure within the central 60° of view of the individual. Typically, the array of photodetector devices needs to be 40 cm wide and includes from 4 to 10 photodetectors in each sub-array. Suitable photodetectors for use in the photodetector array of the present invention include silicon, InGaAsP, GaAs.

Figure 2A:
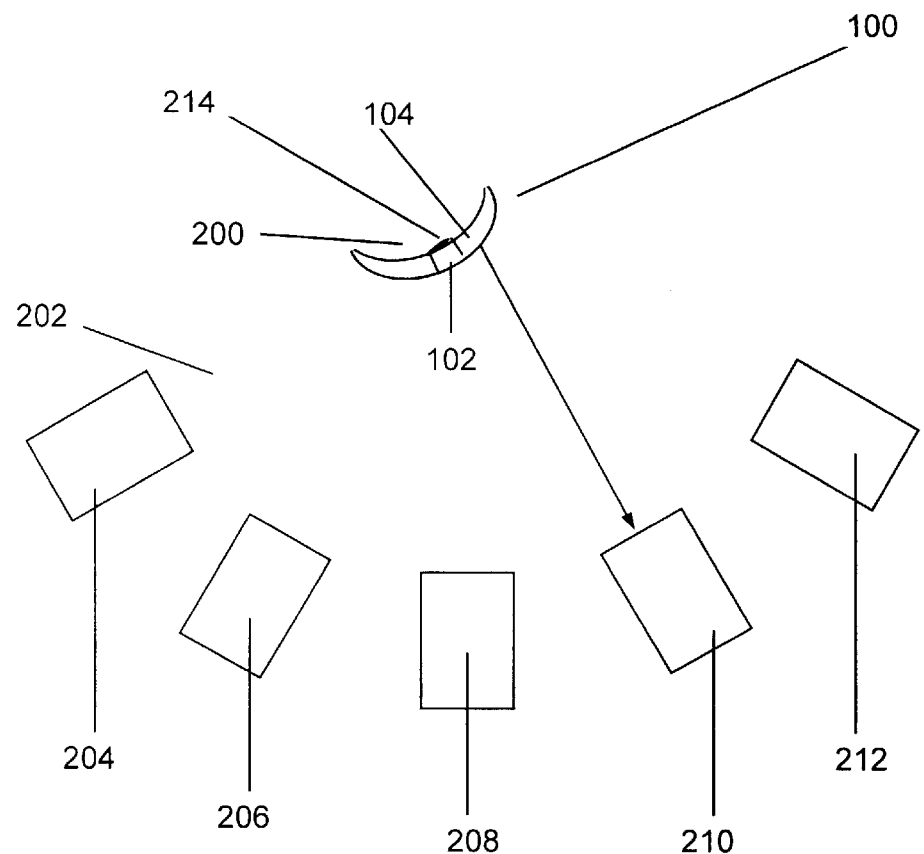
FIG. 2A illustrates in simplified schematic form a horizontal layer of a three dimensional array of paired photodetector devices as used in the method of the present invention.
Figure 2B:
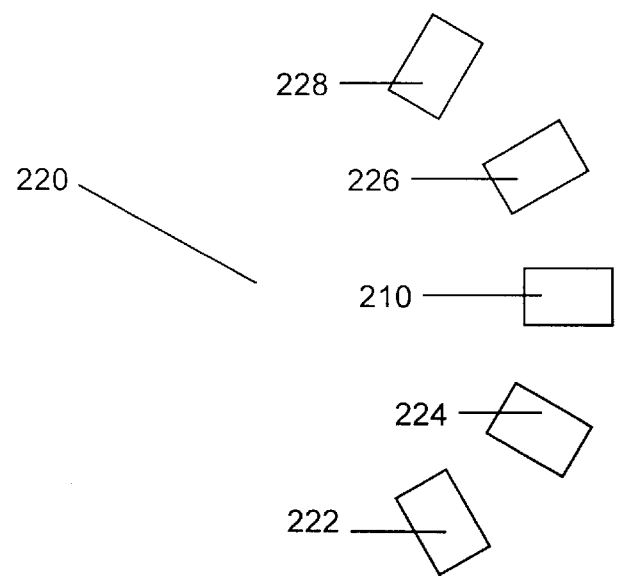
FIG. 2B illustrates in simplified schematic form a vertical layer of the three dimensional array of FIG. 2A.
Figure 3:
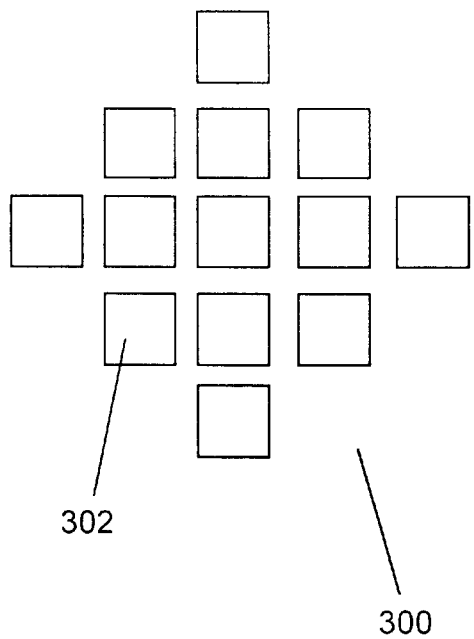
FIG. 3 illustrates in schematic form a three dimensional array of paired photodetector devices of one embodiment of the present invention.
Figure 4:
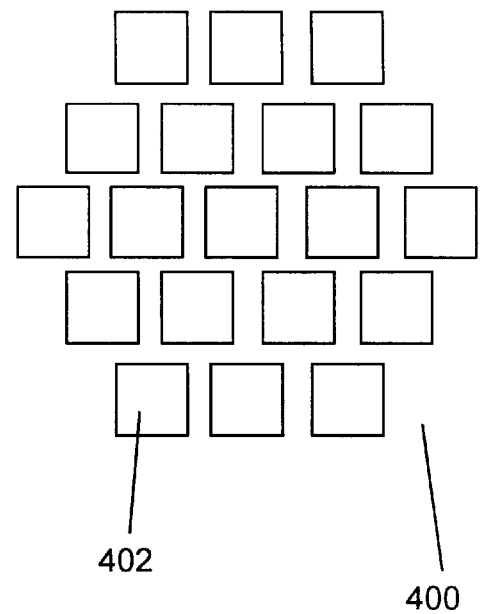
FIG. 4 illustrates in schematic form a three dimensional array of paired photodetector devices of one embodiment of the present invention.

As an eye of an individual moves, each of the photodetectors of the sub-array for that eye will in turn detect an infrared wavelength filtered by the Fresnel rings of the contact lens for that eye as the sight line of the eye/contact lens aligns itself with a particular photodetector. FIG. 2A shows how the method of the invention works for one eye 200 of an individual. Although for the sake of simpliicty, FIG. 2A only shows how the method of the present invention is practiced for one eye, the method of the present invention is capable of testing both eyes of an individual both independently and simultaneously. Also for simplicity only a portion of the array is shown in FIG. 2A and the objects and the distance relationship between objects are not shown to scale in FIG. 2A. For example, although only five paired photodetector devices are shown in FIG. 2A, in actuality, there will generally be more than five paired photodetector devices in the photodetector array and the array will be located considerably farther away from the individual's eye than is shown in FIG. 2A. Furthermore, FIG. 2A only illustrates one layer of an array of paired photodetector devices that exists in three dimensions. FIG. 2A illustrates one horizontal layer of an array 202 of paired photodetector devices 204, 206, 208, 210 and 212 are set-up at a distance, preferably about ⅓ m, from the surface of an individual's eye 200 and pupil 214 on which is mounted contact lens 100 of the present invention. Each of the paired photodetector devices 204, 206, 208, 210, and 212 include two photodetectors (not visible in FIG. 2A), one photodetector for detecting an infrared wavelength filtered by exterior region 104 of contact lens 100 mounted on the individual's eye 200 and one for detecting an infrared wavelength filtered by an exterior region of a contact lens mounted in the individual's left eye (not shown). Although only one horizontal layer of paired photodector devices is shown in FIG. 2A, there are preferably several layers of paired photodetector devices above and below the layer shown in FIG. 2A so that the array of the present invention constitutes a three dimension array of paired photodetector devices. For example, FIG. 2B shows a vertical layer 220 of paired photodetector devices 222, 224, 226, and 228 that are located in horizontal layers above and below paired photodetector device 210. As shown, photodetector devices 222, 224, 226 and 228 are tilted with respect to photodetector device 210 so that photodetector devices 222, 224, 226 and 228 will better line up with a individual's eye. The three dimensional arrays of the present invention may have a variety of arrangements. For example, FIG. 3 shows a three-dimensional array 300 of paired photodetector devices 302 in which photodetector devices 302 are arranged in horizontal and vertical layers. FIG. 4 shows a three-dimensional array 400 in which photodetector devices 402 are in a staggered configuration. Although only a few simplified arrangements of the three dimensional arrays are shown, the present invention also encompasses various other types of three dimensional arrays. Preferably, whatever the array shape, the photodetector devices are angled toward the individual's eyes as shown in FIGS. 2A and 2B.

As the individual's eye 200 and pupil 214 rotate the Fresnel rings in exterior region 104 reflect light, in turn, towards paired photodetector devices 204, 206, 208, 210, and 212. FIG. 2A illustrates a paired photodetector device 210 being in alignment with contact lens 100 and a photodetector (not visible in FIG. 2A) in paired photodetector device 210 detecting infrared light reflected and filtered by exterior region 104. Because the contact lenses of the present invention give each eye of the individual a different "infrared profile" the positions of both eyes may be detected both independently and simultaneously using the method of the present invention. Although for simplicity, only the detection of horizontal rotational movement of an individual's eye is shown in FIG. 2A, it should be appreciated that the three-dimensional array of the present invention also detects vertical and diagonal rotational movement of an individual's eye as well.

Figure 5:
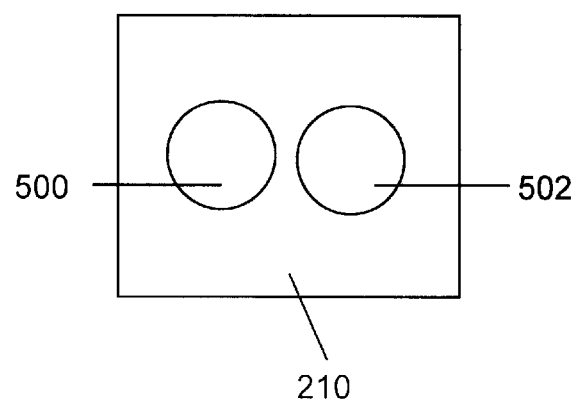
FIG. 5 is a front view in schematic form of a paired photodetector device of FIGS. 2A and 2B.

FIG. 5 shows in greater detail paired photodetector device 210 which is similar in structure to paired photodetector devices 204, 206, 208 and 210. Photodetector 210 includes a photodetector 500 for detecting infrared light filtered by a contact lens on an individual's right eye and a photodetector 502 for detecting infrared light filtered by a contact lens on the individual's left eye. Photodetectors 500 and 502 may be angled horizontally with respect to each other to better line up with the right and left eyes, respectively, of the individual being tested.

As an individual's eye lines up with each of the photodetectors of the present invention, the position of that eye is recorded by a convention digital recording device, such as a computer that is connected to each of the photodetectors. Based on the recorded positions of the eye over a set period of time, the point to point velocity of the eye may then be calculated using a computational means, such as a computer. Also, a topographical map of eye velocity may also be created using the position and velocity data for each eye using a computational means, such as a computer.

Although the array of paired photodetectors shown in FIG. 3 is in three dimensions, the method of the present invention also encompasses the possibility of having an array of photodetectors in only two dimensions to just track movements of an individual's eye in a particular vertical or horizontal plane.

Because the maximum saccadic velocity for a human eye is around 500°/sec, the photodetectors of the present invention preferably have internal switches which allow the photodetectors to be turned on and off quickly so that they do not miss a movement of an individual's eye.

The method of the present invention allows for an extraocular muscle functioning test (EOMT) that has the following advantages over prior extraocular muscle functioning tests: 1. An EOMT that shows the position to position changes in eye velocity which may later be plotted in topographic fashion for each eye. 2. An EOMT that shows differences in position of each eye relative to the other eye over the entire central 60° of eye movement in all directions at 1 cm intervals. 3. Allows for comparisons of data maps for each eye with a large internal database that would provide "finger print" recognition and a differential diagnosis.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A method for measuring the movement of an individual's eye comprising the steps of:
   mounting a first infrared filter in a first eye of an individual, said first infrared filter filtering infrared light at a first wavelength;
   mounting a second infrared filter in a second eye of an individual, said second infrared filter filtering infrared light at a second wavelength;
   detecting infrared light of said first wavelength filtered by said first infrared filter by a first sub-array of photodetectors as the first eye of the individual rotates; and
   detecting infrared light of said second wavelength filtered by said second infrared filter by a second sub-array of photodetectors as the second eye of the individual rotates.

2. The method of claim 1, wherein each of said first and said second infrared filters comprises at least one Fresnel ring located in a contact lens and concentrically surrounding a central clear zone in said contact lens.

3. The method of claim 1, wherein each of said first and said second infrared filters comprises at least two concentric Fresnel rings located in a contact lens and concentrically surrounding a central clear zone in said contact lens.

4. The method of claim 1, wherein said first and second sub-arrays of photodetectors comprises an array of paired photodetector devices.

5. The method of claim 4, wherein said array of photodetectors comprises at least 4 paired photodetector devices.

6. The method of claim 4, wherein said array of paired photodetector devices comprises a three dimensional array of paired photodetector devices.

7. The method of claim 6, wherein said array of paired photodetector devices is staggered in at least the horizontal direction.

8. The method of claim 6, wherein said array of paired photodetector devices is staggered in at least the vertical direction.

9. The method of claim 1, wherein both of said detecting steps are performed simultaneously.

10. The method of claim 1, further comprising the step of recording in digital sequence the position of said first and second eyes of the individual based on the time and position at which said photodetectors in said two sub-arrays of photodetectors detect infrared light from said first and second infrared filters, respectively.

11. The method of claim 10, further comprising the step of calculating the point to point velocity change of each eye based on said recording step.

12. The method of claim 11, further comprising forming topographic velocity maps for each eye based on the information obtained from said recording step and said calculating step.

13. The method of claim 1, wherein said first sub-array of photodetectors and said second sub-array of photodetectors are located about ⅓ m from the individual or greater.

14. A contact lens comprising:
   a lens having a central clear zone; and
   at least one Fresnel ring circumferentially surrounding said central clear zone and filtering at least one wavelength of infrared light.

15. The contact lens of claim 14, wherein said at least one Fresnel ring comprises at least two concentric Fresnel rings.

* * * * *